(12) United States Patent
Heffez

(10) Patent No.: US 6,896,662 B2
(45) Date of Patent: May 24, 2005

(54) METHOD FOR LORDOSIS ADJUSTMENT FOR TREATING DISCOMFORT IN, OR ORIGINATING IN, THE CERVICAL SPINE REGION

(76) Inventor: Dan S. Heffez, 2711 Colfax, Evanston, IL (US) 60201

( * ) Notice: Subject to any disclaimer, the term of this patent is extended or adjusted under 35 U.S.C. 154(b) by 148 days.

(21) Appl. No.: 10/374,658

(22) Filed: Feb. 26, 2003

(65) Prior Publication Data

US 2004/0167448 A1 Aug. 26, 2004

(51) Int. Cl.$^7$ .................................................. A61F 5/00
(52) U.S. Cl. ............................................................. 602/19
(58) Field of Search ........................ 602/5, 19; 128/845, 128/846, 869, 870, 876

(56) References Cited

U.S. PATENT DOCUMENTS

| | | |
|---|---|---|
| 2,813,526 A | 11/1957 | Beebe |
| 4,285,336 A | 8/1981 | Oebser et al. |
| 5,211,163 A | 5/1993 | Mortenson |
| 5,259,831 A | 11/1993 | LeBron |
| 5,295,947 A | 3/1994 | Muncy |
| 5,433,697 A | 7/1995 | Cox |
| 5,437,614 A | 8/1995 | Grim |
| 5,492,496 A | 2/1996 | Walker |
| 5,547,462 A | 8/1996 | Lanigan et al. |
| 5,632,723 A | 5/1997 | Grim |
| 5,690,609 A | 11/1997 | Heinze, III |
| 5,718,670 A | 2/1998 | Bremer |
| 5,911,697 A | 6/1999 | Biedermann et al. |
| 6,165,147 A | 12/2000 | Morrow |
| 6,237,602 B1 | 5/2001 | Nickels et al. |
| 6,331,170 B1 | 12/2001 | Ordway |

*Primary Examiner*—Michael A. Brown
(74) *Attorney, Agent, or Firm*—Schiff Hardin LLP

(57) ABSTRACT

A method for alleviating neck discomfort includes the steps of removably attaching at least one pad to a rigid posterior force applicator to set a thickness of a combination of the pad (or pads) and the posterior force applicator to produce lordosis adjustment in a patient experiencing neck discomfort so as to cause a neutral head and neck orientation of that patient, disposing an anterior force applicator, having a substantially continuous, rigid frame with an open central region, on the patient with an upper region of the frame approximately at a lower costal region of the patient and a lower portion of the frame approximately at the symphisis pubis of the patient, and connecting the anterior force applicator to the posterior force applicator with straps at opposite lateral sides thereof with the posterior force applicator approximately at the L3 vertebra of the patient to effect such lordosis adjustment and said neutral head and neck orientation.

8 Claims, 6 Drawing Sheets

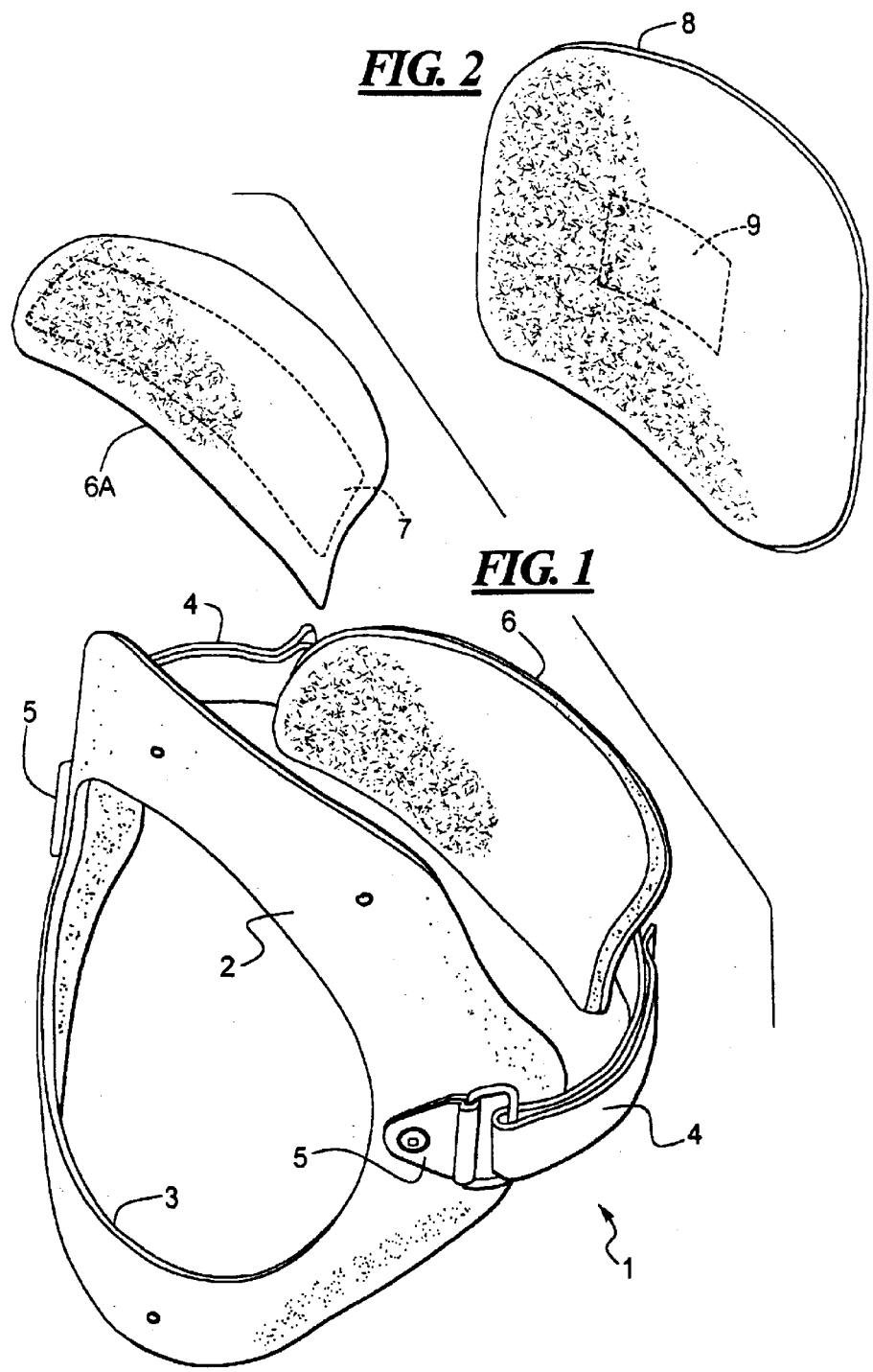

METHOD FOR LORDOSIS ADJUSTMENT FOR TREATING DISCOMFORT IN, OR ORIGINATING IN, THE CERVICAL SPINE REGION

BACKGROUND OF THE INVENTION

1. Field of the Invention

The present invention is directed to a method for effecting lordosis adjustment in order to treat discomfort, or pain in or originating in the cervical spine region.

2. Description of the Prior Art

Various types of body-worn braces or support are known for providing mechanical assistance to aid weak or ineffectual muscles or the treatment of the various types of back disorders and discomfort. Examples of such known orthotic braces are described in U.S. Pat. Nos. 5,911,697; 5,718,670; 5,690,609; 5,547,462; 5,433,697; 5,295,947; 5,259,831; 4,285,336 and 2,813,526.

These devices, and others of their type, have in common a design and structure that are specifically adapted to provide some type of mechanical support, primarily in the lumbar region, which would normally be provided by a healthy muscular or skeletal system, but which in certain occasions, due to disease or injury, is lacking or in need of augmentation. In general, these types of known devices can be considered as "stiffening" the lumbar region for the purpose of achieving this result.

Certain of these devices also are specifically designed to constrict or confine movement of the lumbar region for cases where such movement induces pain or discomfort, or aggravates the particular back disorder being treated.

In a healthy person with good posture, the spinal column exhibits a curvature toward the abdomen (anterior curvature) as well as a curvature in the upper back region and into the neck region. The normal concave curvature of the lumbar spine and cervical spine is referred to as lordosis. Because of the interconnectedness of the vertebrae forming the spinal column, it is known that abnormal curvature of the spinal column in one region can produce abnormal curvature in another region.

The known braces or supports of the type described above, by stiffening or confining the lumbar region, may have an incidental effect on lumbar lordosis, but they are not designed to intentionally adjust or redirect lumbar lordosis as their primary function. Moreover, conventional braces and supports of the above type are designed for treating particular disorders of the lumbar region and are not designed to intentionally effect or alter other regions of the spinal column, such as the cervical spine region.

Many supports and braces are also known for providing similar mechanical stiffening and confinement in the cervical spine region. The conventional approach for patients suffering from neck pain or other neck disorders has been to prescribe the use of such neck or cervical spine braces, which interact with the patient directly in the cervical spine region.

SUMMARY OF THE INVENTION

It is an object of the present invention to provide a method for alleviating neck pain or discomfort in, or originating in, the cervical spine region without the necessity of using a conventional neck brace.

The above object is achieved in accordance with the principles of the present invention in a method wherein lordosis adjustment in the lumbo-sacral region is undertaken in a manner and to an extent to produce a neutral orientation of the head and neck on the spinal column.

The inventive method includes the steps of removably attaching at least one pad to a rigid posterior force applicator to set a thickness of a combination of the pad (or pads) and the posterior force applicator to produce lordosis adjustment in a patient experiencing neck discomfort so as to cause a neutral orientation of the cervical spine of that patient, disposing an anterior force applicator, having a substantially continuous, rigid frame with an open central region, on the patient with an upper region of the frame approximately at a lower costal region of the patient and a lower portion of the frame approximately at the symphisis pubis of the patient, and connecting the anterior force applicator to the posterior force applicator with straps at opposite lateral sides thereof with the posterior force applicator approximately at the L3 vertebra of the patient to effect such lordosis adjustment and the neutral cervical spine orientation.

The method is implemented with an appliance adapted to be worn by such a patient in the lumbo-sacro region which has a design and structure specifically for effecting lordosis adjustment in the lumbo-sacro region in a manner which has the consequence of causing a neutral orientation of the cervical spine region, thereby alleviating the neck discomfort or pain experienced by the patient.

The inventive method is based on the recognition that by making a lordosis adjustment in the lumbo-sacro region, by the application of force vectors to the back and abdomen at specified locations, in order to replicate as closely as possible normal, healthy lordosis, this will necessarily result in the spinal column in the cervical spine region also exhibiting a lordosis restored to that of a healthy person with good posture, or at least will significantly improve lordosis in the cervical spine region. The appliance worn by the patient in the lumbo-sacro region in the preferred embodiment of the method has a structure and design for producing the aforementioned force vectors at specified locations in order to restore healthy lordosis for the purpose of alleviating discomfort in, or originating in, the cervical spine region. The necessity of wearing a discomforting and a cumbersome neck brace is therefore avoided. Moreover, because the method for lordosis adjustment is not intended involve bracing or support of the conventional type described initially, the structure and bulk of the appliance for implementing the method are relatively minimal and lightweight, and therefore it can be worn in a relatively unobtrusive manner under clothing.

The appliance for implementing the method includes an anterior portion, serving as the aforementioned anterior force applicator, with a large central opening therein and a surrounding frame that is adapted to be worn approximately over the abdomen. This anterior portion of the appliance is connected by straps to a posterior portion, serving as the aforementioned posterior force applicator, which is designed to be relatively short in vertical height to cover only approximately the L2 through L4 vertebrae (the peak lordotic curve occurs at the L3 vertebra). The short vertical height of the posterior portion of the appliance is possible because it is not intended in the inventive method to perform bracing or stiffening.

The aforementioned openness of the anterior portion is important for implementing the method to achieve the intended lordosis adjustment. If the anterior portion of the appliance were solid, i.e., without a central opening, the abdominal resistance would be too large and the force vectors produced by the posterior portion of the appliance would have little or no effect.

The degree of lordosis adjustment is created by the step of employing one or more pads that are removably attached to and carried by the posterior portion of the appliance. It would be possible for the posterior portion of the appliance to be customized to have a specified curvature adapted to a particular patient to, at least to a certain extent, produce the desired amount of lordosis adjustment for that patient. In order to make the method more universally applicable for a large number of patients, however, a standardized posterior portion, or at least only a few standardized posterior portions with respectively different curvatures, is/are employed, and the amount of lordosis adjustment is achieved by adding the step of pads to this standardized posterior portion, as needed. The more pads that are added, the greater the amount of lordosis adjustment that can be achieved. The pads can be attachable one on top of the other by a hook-and-loop system, or by any other appropriate system allowing temporary attachment. In general, the posterior portion itself will provide only a slight lordosis adjustment, and it is the use of one or more pads which is intended to produce the prescribed amount of lordosis adjustment for alleviating the particular discomfort in the cervical spine region of a given patient.

The anterior portion of the appliance, by virtue of its shape and extent and its open center, is intended to accomplish the method step of applying force vectors at two basic impact regions. A lower point of impact is approximately at the symphisis pubis, and the upper point of impact is in the lower costal margin, i.e., approximately at the lower edge of the rib cage. The force vectors applied in the lower costal margin are preferably applied at two impact points which are spaced from each other, so that a total of three impact points, approximately located at respective vertices of a triangle, are produced by the anterior portion of the appliance.

As noted above, a benefit of the method is that the appliance for implementing the method does not necessarily need to be customized to the anatomy of the person by whom it will be worn, since the desired lordosis adjustment is achieved by the appropriate selection and use of one or more pads attached to the posterior portion of the appliance. Nevertheless, the appliance can be manufactured in several basic sizes, such as a size adapted to be worn by a child and a size adapted to be worn by an adult. Intermediate sizes also could be available, if needed.

DESCRIPTION OF THE DRAWINGS

FIG. 1 is a perspective view of a first embodiment of an appliance for implementing lordosis adjustment in accordance with the inventive method, showing one additional pad for attachment to the posterior portion.

FIG. 2 illustrates a pad for use in a second embodiment of an appliance for implementing lordosis adjustment in accordance with the inventive method.

DESCRIPTION OF THE PREFERRED EMBODIMENTS

Figure 3:
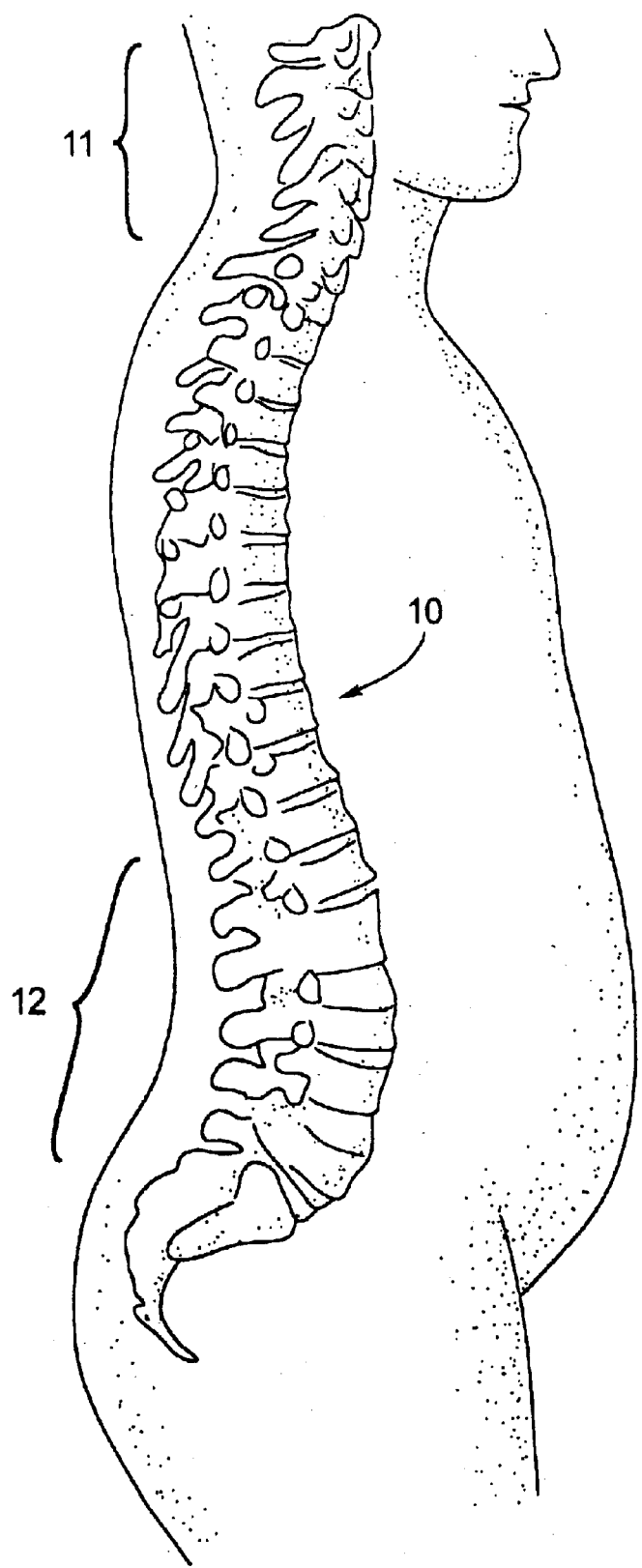
FIG. 3 schematically illustrates normal spinal column lordosis which represents a target to be adjusted by the inventive method to relieve neck discomfort in, or originating in, the cervical spine region.

A lumbo-sacro support is used in a preferred embodiment of the method to maintain or accentuate the lumbar lordosis in order to promote a neutral orientation of the head or neck on the upper body, for the purpose of alleviating neck discomfort, or in general pain or discomfort in, or originating in, the cervical spine region without the necessity of wearing a neck brace or support. The promotion of the proper posture of the head or neck on the upper body is achieved by appropriate lordosis adjustment in the lumbar region through the action of the standing and righting reflexes which normally maintain proper erect body posture. The importance of such a neutral neck or cervical spine position, as opposed to a position of flexion or extension, follows from the relationship between the nerve roots and the spinal cord to the bony spinal canal and neural foramina. The anteroposterior dimension of the spinal canal and neural foramina changes with the orientation of the neck. Mild spinal flexion enlarges the anteroposterior diameter, while neck extension narrows the anteroposterior diameter. In cases of narrowing of the spinal canal (stenosis) such changes in the diameter of the spinal canal can determine whether the spinal cord or the nerve roots are compressed, irritated or traumatized, as well as determining the extent of such compression, or irritation or trauma. Maintaining a neutral cervical spine posture can minimize spinal cord or nerve root irritation, and in some cases eliminate it completely. Poor lumbar and thoracic posture necessitates compensatory cervical alignment in order to allow the person experiencing the poor posture to be able to look straight ahead.

Improper cervical lordosis accentuates cervical extension, and as a result narrows the spinal canal and neural foramina. By encouraging and ensuring proper lumbar lordosis in the sitting or standing position, the maintenance of a neutral neck orientation is promoted and therefore is useful in the treatment of conditions that result in or from spinal canal narrowing. Similarly, treatment or manipulation of the lumbar spine designed to maintain proper lumbar lordosis is expected to promote neutral cervical alignment and orientation, and can be beneficial to the management of conditions that result in or from spinal canal narrowing.

Examples of conditions which can be effectively treated or managed by the inventive method to optimize cervical posture are as follows:

Congenital cervical spinal stenosis which does not warrant surgical decompression.

Cervical spinal stenosis secondary to the protrusion of bone parts, bulging or herniated intervertabral disc, thickened ligamentum flavum or ossified posterior longitudinal ligament which does not warrant surgical decompression.

Following cervical spine surgery, when maintaining proper posture is important for the prevention of secondary spinal deformity or intervertebral disc degeneration.

Arthritides which damage the joints and supportive structures of the spine and that might contribute to poor cervical posture.

Cervical myelopathy due to cervical spinal cord compression when the spinal cord compression is of clinical significance, primarily when the neck is positioned in extension, and when neither the severity of myelopathy or spinal cord decompression warrants surgical intervention.

Cases of fibromyalgia syndrome, when these are associated with findings of myelopathy and mild spinal stenosis.

Cases of the Chiari I malformation in which neck extension would provoke an accentuation of compression of the brain stem and spinal cord secondary to increased herniation of the cerebellar tonsils through the foramen magnum at the base of the skull.

Cervical radiculopathy or nerve root irritation due to stenosis of a neural foramen if the stenosis is of clinical significance, primarily when the patient's neck is in extension and when surgical decompression is not required.

Examples of symptoms which may arise from the above-mentioned anatomical or pathological conditions, and therefore may be amenable to a treatment strategy involving optimizing cervical spine posture using the inventive method, are as follows:

Headache, especially occipital, vertex and retroocular headaches—cervicogenic headaches.

Pain including neck, interscapular, subscapular, midline spinal, lumbar, arm or leg pain.

Certain facial pains including pains in the distribution of temperomandibular joint, when believed to be of cervicogenic origin.

Dizziness or vertigo of spinal origin.

Limb or facial numbness or tingling.

Impaired balance when standing or walking.

Disturbance of bowel motility including diarrhea and constipation and irritable bowel syndrome when diagnosed as being of neurogenic, spinal origin.

Urinary frequency, urgency or incontinence when diagnosed to be of neurogenic cervical spinal origin.

Physical muscular fatigue when diagnosed as arising due to cervical spinal cord compression or irritation; such fatigue is frequently described by patients with fibromyalgia, chronic fatigue syndrome and cervical myelopathy.

Otological symptoms such as tinnnitus, hyperacusis, or pressure in the ears, diagnosed to be of cervicogenic origin.

Autonomic disturbances such as tachyarrythmias, hypertension, hypotension, impaired circulation in the hands and feet, Postural Orthostatic Tachycardia Syndrome and Neurally Mediated Hypotension, if diagnosed to be due to a cervical neurogenic mechanism.

Blurred or double vision diagnosed to be of a cervical neurogenic origin.

Limb weakness diagnosed to be of a neurogenic, cervical spinal origin.

In general, symptoms as exemplified above can be characterized as symptoms arising from spinal cord and/or nerve root compression, due to misalignment of the cervical spine.

The above conditions and symptoms can be alleviated by an appliance for implementing the inventive method, as shown in FIG. 1. The appliance 1 has an anterior portion 2 and a posterior portion 6 connected by belts or straps 4. Each strap 4 proceeds through a retainer 5 attached at one side of the anterior portion 2. In the embodiment shown in FIG. 1, each strap 4 has a hook and loop surface, so that when the free end of each strap 4 is fed through the retainer 5, the strap 4 can be folded over on itself to set and fix a desired length of each strap 4 to accommodate a particular patient. The opposite end of each strap 4 is affixed in a suitable manner to the anterior portion 6.

As discussed in more detail below, the anterior portion 2 has a central opening 3 and is designed, for implementing the method, to be worn approximately over the abdomen, but without pressing directly on the central region of the abdomen.

As also shown in FIG. 1, the appliance 1 includes one or more pads 6A, which is/are temporarily attachable to the posterior portion 6 by a temporary attachment 7 such as hook-and-loop arrangement. The posterior portion 6 has padding or malting on the side thereof that is worn against the body. Although only one pad is shown in FIG. 1, multiple additional pads, corresponding to the pad 6A, can be used as needed to implement the method step of producing the necessary total thickness of the combination of the anterior portion 6 and pad or pads 6A, to produce the desired lordosis adjustments for alleviating symptoms or conditions of the type described above.

As also noted above, since it is not the purpose of the inventive method 1 to perform bracing or support, the height of the posterior portion 6 of the appliance 1 is intentionally kept relatively short. For some conditions or symptoms, however, it may be desirable to slightly enlarge the height of the posterior portion 6, in which case a pad 8 such as shown in FIG. 2 can be used, which has a larger height than the pad 6A. Like pad 6A, the pad 8 can be attached to the posterior portion 6 with a temporary attachment 9, such as a hook-and-loop arrangement. Although not necessary, the posterior portion for use with the pad 8 can be enlarged to a size approximating the size of the pad 8. As noted above, however, it is not the overall size (area) of the pads which is effective for the intended purpose in the appliance 1, but rather the step of setting an accumulated thickness to produce the desired lordosis adjustment.

Figure 4:
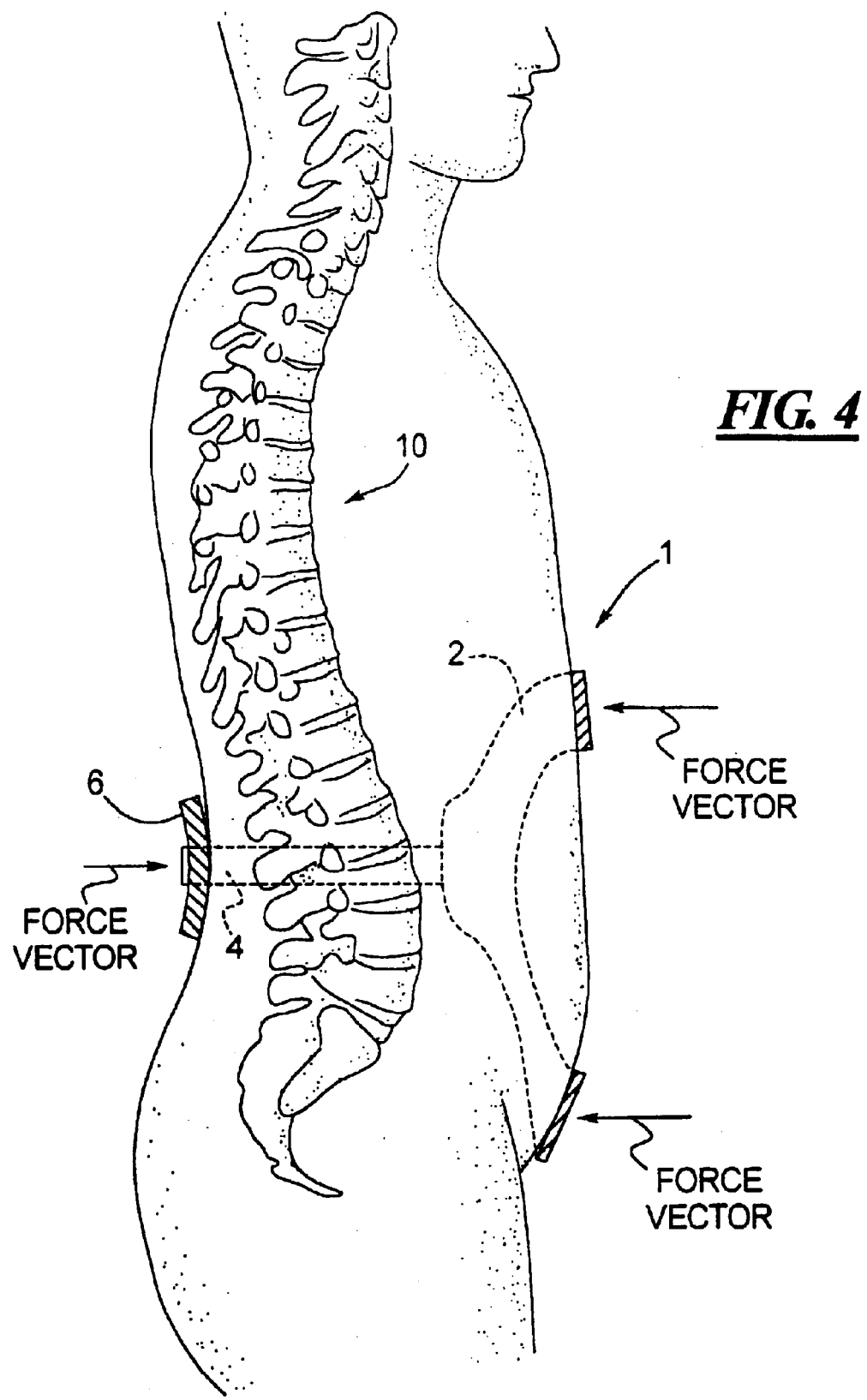
FIG. 4 is a sectional view illustrating the forces generated when the inventive method for implementing lordosis adjustment in accordance with the inventive method is worn by a patient as shown in FIG. 3.

FIG. 3 is a schematic, sagittal view of a patient experiencing normal lordosis in the lumbar region 12 of the spinal column 10. Treatment of an absence of this normal lordosis by wearing the appliance 1 in accordance with the method is schematically indicated in FIG. 4, wherein the force vectors applied at upper and lower regions of the abdomen by the anterior portion 2, and at the lumbar region by the posterior portion 6, as illustrated. As can be seen in comparison to FIG. 3, the lordosis in the lumbar region 12 is restored by wearing the appliance 1, and this in turn slightly elevates the head on the neck, thereby restoring the cervical region to a neutral orientation on the upper body.

Figure 5:
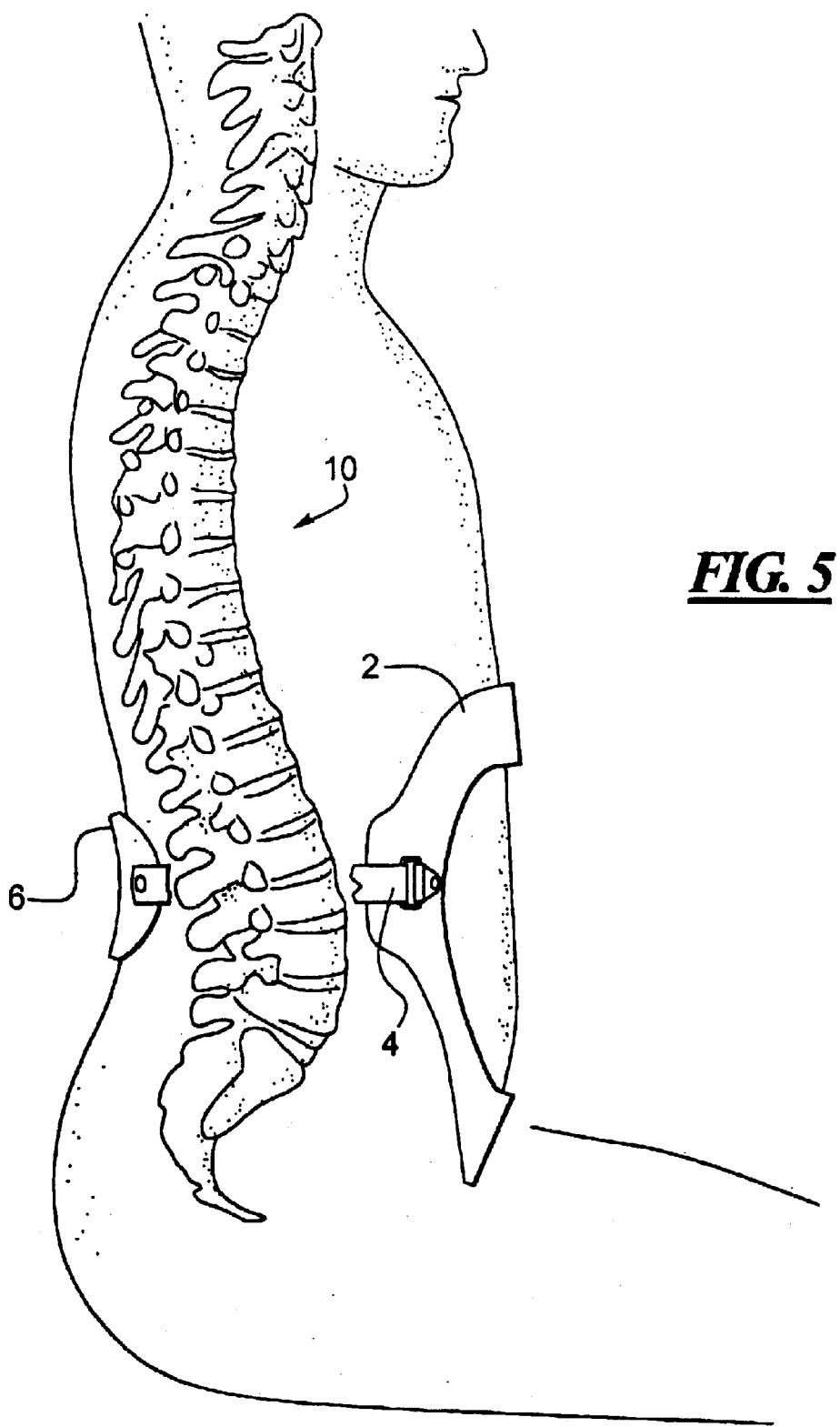
FIG. 5 illustrates the lordosis adjustment achieved by a seated person wearing an appliance for implementing the inventive method.
Figure 6:
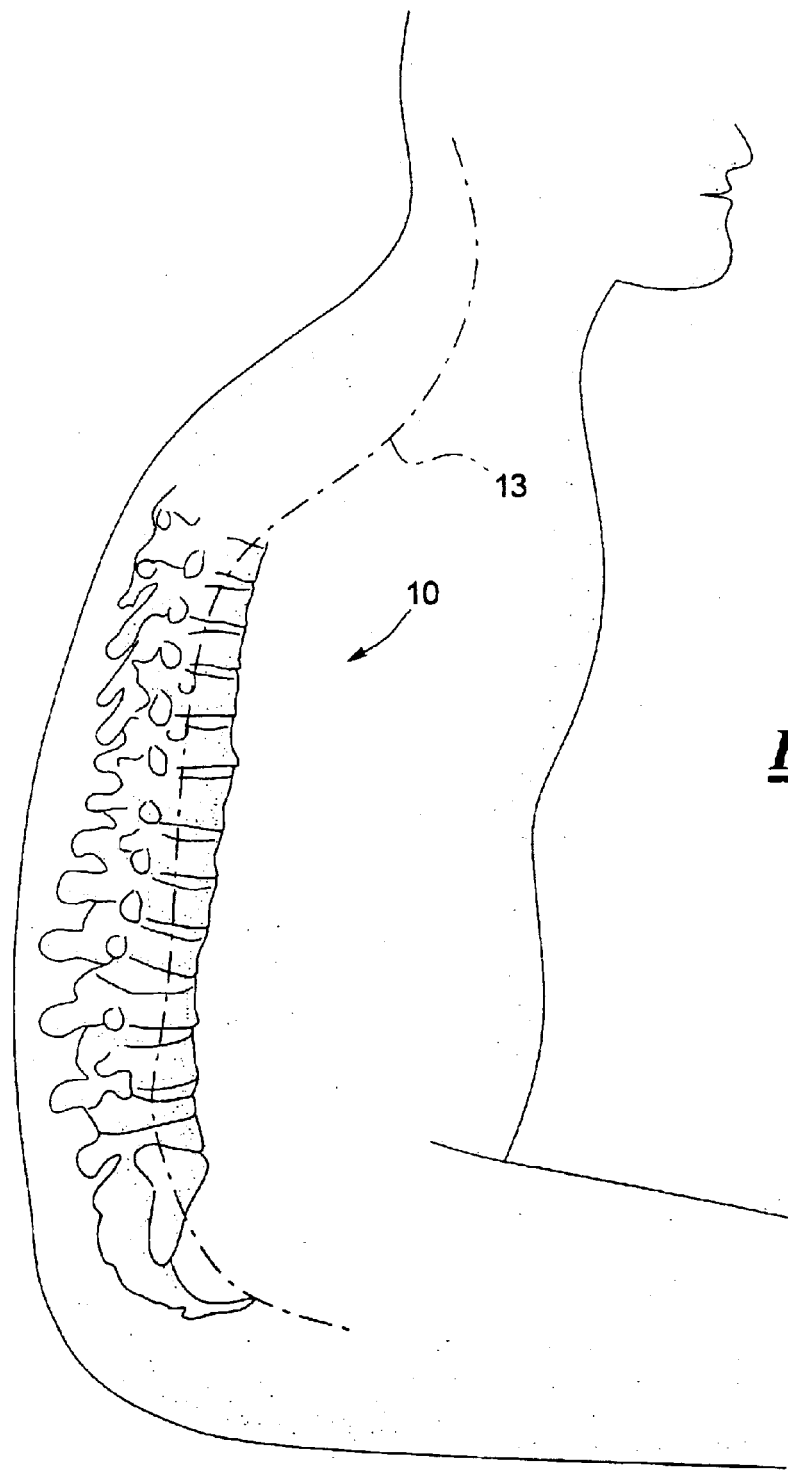
FIG. 6 illustrates spinal column lordosis (or absence thereof) as would occur in the seated person not treated by the inventive method.

A similar situation is shown for a seated patient Wearing the appliance 1 in accordance with the method in FIG. 5. Without wearing such an appliance, the seated person would most likely exhibit the posture indicated by the dot and dash line 13 in FIG. 6. As can be seen in FIG. 5, proper posture, and neutral head and neck (cervical spine) orientation, are maintained and achieved by the appliance 1 worn by the seated person.

Figure 7:
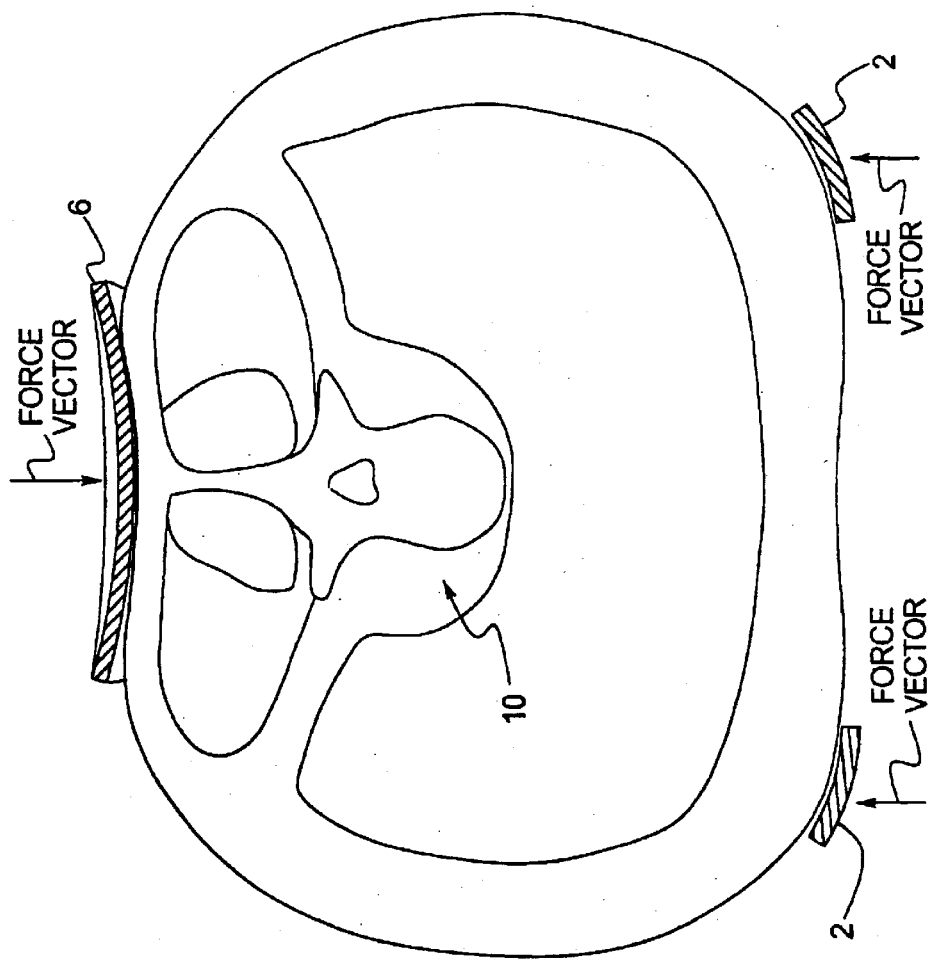
FIG. 7 is a schematic axial section through the lumbar region of a person wearing an appliance for implementing the inventive method.

The method step of applying force vectors is achieved by the appliance 1 as shown in a schematic axial view in FIG. 7. The force vectors indicated at the bottom of FIG. 7 are applied approximately at the locations indicated by circles in the upper region of the anterior portion 2 in FIG. 1. The lower force vector (shown in FIG. 4) is applied approximately at the location indicated by the circle in the lower region of the anterior portion 2 in FIG. 1. As noted above, the force vectors applied in the inventive method by the anterior portion 2 in the upper region are at spaced-apart locations in the lower costal margin, and the lower force vector applied by the anterior portion 2 is approximately at the symphisis pubis. Such a three-point impact arrangement of the force vectors produced by the anterior portion 2 (in combination with the oppositely-directed force vector produced by the posterior portion 6) is specifically designed and positioned for achieving the desired lordosis adjustment for alleviating conditions and symptoms of the type described above.

The pad or pads 6A (and 8) are composed of a padding material which may be on a stiffer backing or carrier, such as a plastic carrier. The padding material should be sufficiently compressible so as to be comfortable for the patient to wear, however, it should not be so compressible that the desired force vectors cannot be produced when the appliance is worn with the straps 4 tightened to a comfortable length. Compressed fibers forming a mat of padding material are preferable, primarily because they are simplest to manufacture and maintain. Such a mat can simultaneously serve as part of the hook-and-loop temporary attachment. Other versions are possible, however, such as a fluid-filled cushion, or an inflatable cushion which can be inflated to the desired thickness as needed.

Although other modifications and changes may be suggested by those skilled in the art, it is the intention of the inventor to embody within the patent warranted hereon all changes and modifications as reasonably and properly come within the scope of his contribution to the art.

I claim as my invention:

1. A method for alleviating discomfort in, or originating in, the cervical spine region of a patient comprising the steps of:

removably attaching at least one pad to a rigid posterior force applicator to set a thickness of a combination of said pad and said posterior force applicator to produce a selected lordosis adjustment in a patient experiencing discomfort in, or originating in, the cervical spine region to cause a neutral cervical spine orientation of said patient;

disposing an anterior force applicator, having a substantially continuous, rigid frame with an open central region, on said patient with an upper region of said frame approximately at a lower costal region of said patient and a lower portion of said frame approximately at the symphisis pubis of said patient; and connecting said anterior force applicator and said posterior force applicator on said patient with straps at opposite lateral sides thereof to position said posterior force applicator approximately at the L3 vertebra of said patient to effect said lordosis adjustment and said neutral cervical spine orientation, with substantially no therapeutic bracing and support of said patient by said anterior and posterior force applicators.

2. An method as claimed in claim 1 comprising employing a rigid element as said posterior force applicator having a structural height substantially coextensive with one vertebra above and one vertebra below said L3 vertebra.

3. A method as claimed in claim 1 comprising applying respective force vectors with said anterior force applicator at two spaced-apart locations in said lower costal region and a location at said symphisis pubis.

4. A method as claimed in claim 1 comprising removably attaching said at least one pad to said posterior force applicator with a hook-and-loop fastening arrangement.

5. An method as claimed in claim 1 comprising employing a rigid element as said posterior force applicator having a structural height substantially coextensive with one vertebra above and one vertebra below said L3 vertebra.

6. A method as claimed in claim 1 comprising applying respective force vectors with said anterior force applicator at two spaced-apart locations in said lower costal region and a location at said symphisis pubis.

7. A method as claimed in claim 1 comprising removably attaching said at least one pad to said posterior force applicator with a hook-and-loop fastening arrangement.

8. A method for alleviating discomfort in, or originating in, the cervical spine region of a patient comprising the steps of:

for a patient experiencing discomfort in, or originating in, the cervical spine region, diagnosing and prescribing a selected degree of lumbar lordosis adjustment to cause a neutral cervical spine orientation of said patient;

removably attaching at least one pad to a rigid posterior force applicator to set a thickness of a combination of said pad and said posterior force applicator to produce a said selected lumbar lordosis adjustment in said patient to cause said neutral cervical spine orientation of said patient;

disposing an anterior force applicator, having a substantially continuous, rigid frame with an open central region, on said patient with an upper region of said frame approximately at a lower costal region of said patient and a lower portion of said frame approximately at the symphisis pubis of said patient; and connecting said anterior force applicator and said posterior force applicator on said patient with straps at opposite lateral sides thereof to position said posterior force applicator approximately at the L3 vertebra of said patient to effect said lordosis adjustment and said neutral cervical spine orientation, with substantially no therapeutic bracing and support of said patient by said anterior and posterior force applicators.

* * * * *